United States Patent

Battiston et al.

[11] 3,981,912
[45] Sept. 21, 1976

[54] PROCESS FOR THE PREPARATION OF UNSATURATED CARBOXYLIC ACIDS BY THE CATALYTIC OXIDATION IN GASEOUS PHASE OF THE CORRESPONDING ALDEHYDES

[75] Inventors: Giancarlo Battiston, Baranzate (Milan); Guido Petrini, Milan; Giordano De Alberti, Besnate (Varese); Romano Covini, Milan, all of Italy

[73] Assignee: Montedison S.p.A., Milan, Italy

[22] Filed: Nov. 7, 1975

[21] Appl. No.: 629,986

[30] Foreign Application Priority Data

Nov. 12, 1974 Italy .................................. 29320/74

[52] U.S. Cl. ............................ 260/530 N; 252/443; 252/456; 252/469
[51] Int. Cl.² ........................................ C07C 51/32
[58] Field of Search ................ 260/530 N; 252/443, 252/456, 469

[56] References Cited
UNITED STATES PATENTS 3,567,772   3/1971   Yanagita et al. ................ 260/530 N
3,840,595   10/1974  Grasselli et al. ................ 260/530 N Primary Examiner—Vivian Garner
Attorney, Agent, or Firm—Stevens, Davis, Miller & Mosher

[57] ABSTRACT

A process is disclosed for the preparation of acrylic acid or methacrylic acid, comprising reacting in vapor phase acrolein or methacrolein with molecular oxygen or an oxygen-containing gas, at a temperature between 200° and 350°C, in the presence of a solid catalyst, and with a contact time between 0.5 and .5 seconds, wherein the catalyst consists of molybdenum, vanadium, tin, and one of the elements chromium, nickel, manganese, as well as oxygen chemically combined with the above-indicated elements, the atomic ratios of the elements being represented by the empirical formula:

$$Mo_{12}V_aSn_bX_cO_d$$

wherein:
X is Cr or Ni or Mn;
$a$ is between 0.5 and 10;
$b$ is between 0.4 and 4;
$c$ is between 0.3 and 3.5; and
$d$ is a number that satisfies all the valency requirements of the other elements.

The catalyst may be used on a carrier, and the oxidation reaction may be carried out in the presence of an inert gaseous diluent or water vapor.

3 Claims, No Drawings

PROCESS FOR THE PREPARATION OF UNSATURATED CARBOXYLIC ACIDS BY THE CATALYTIC OXIDATION IN GASEOUS PHASE OF THE CORRESPONDING ALDEHYDES

The present invention relates to a process for the preparation of unsaturated carboxylic acids by the catalytic oxidation in vapor phase, with molecular oxygen or an oxygen-containing gas, of unsaturated aldehydes of low molecular weight, containing more than two carbon atoms. This invention is particularly convenient for producing acrylic acid from acrolein, as well as methacrylic acid from methacrolein.

The process according to this invention is characterized in that the unsaturated aldehyde is oxidized in the presence of a catalyst consisting of molybdenum, vanadium, tin, and one of the elements selected from the class consisting of chromium, nickel and manganese, besides oxygen chemically combined with the above-indicated elements.

The atomic ratios of the elements in the catalyst according to this invention correspond to the following empirical formula:

$Mo_{12}V_aSn_bX_cO_d$, wherein X is Cr or Ni or Mn, and in which $a$ is between 0.5 and 10; $b$ is between 0.4 and 4; $c$ is between 0.3 and 3.5; and $d$ is a number that satisfies all valency requirements of the other elements.

The above-indicated empirical formula simply shows in what atomic ratios the various elements are present in the catalytic composition, and is not intended to represent the actual chemical structure of the catalyst.

The catalyst may be used either without a support, or with a suitable support such as, for instance, silica, alumina, silica-alumina, silicon carbide, pumice, etc.

For the preparation of the catalyst, different processes welll known in the prior art may be used. More particularly, one may combine in an aqueous medium the compounds comprising the various elements and then subject the resulting suspension to evaporation—if desired after the addition of the aforesaid suitable support to the suspension.

The combination of the various components of the catalyst, however obtained, is subjected to calcination in an air stream at a temperature between 350° and 470°C, for a time not less than 2 hours.

The process of this invention may be practiced in any type of reactor suitable for carrying out oxidations in gaseous phase. One may use fixed bed as well as fluid bed reactors per se well known in the art.

The reaction temperature for the oxidation is comprised between 200° and 350°C. The oxidation reaction may be conducted at normal pressure as well as under elevated pressures, for instance up to 10 atm. (absolute).

The contact time, defined as the ratio between the apparent volume of the catalyst and the volume of the fed gas under the reaction conditions in a unit of time, is comprised between 0.5 and 5 seconds.

The concentration of unsaturated aldehyde is comprised between 2.5 and 8% by volume with respect to the feed.

The molar ratio between the oxygen and the unsaturated aldehyde is preferably between 0.5 and 6. The oxygen necessary for the oxidation may be introduced in the pure state; however, air is generally the preferred oxidizing agent.

The oxidation reaction is preferably conducted in the presence of one or more diluents such as nitrogen, carbon dioxide, water vapor, etc. Amongst the possible diluents, water vapor is particularly desirable. The concentration of the water vapor is preferably between 20 and 50% with respect to the feeding mixture.

The following examples are given for the purpose of still more fully describing the invention. They are not intended, however, to limit the scope of the invention.

The terms "conversion" and "selectivity" respectively express:

conversion of the aldehyde in % equals $$\frac{\text{moles of fed aldehyde} - \text{moles of unreacted aldehyde}}{\text{moles of fed aldehyde}} \times 100$$

and selectivity to product in % equals $$\frac{\text{gram atoms of carbon in the product}}{\text{gram atoms of carbon in the reacted aldehyde}} \times 100$$

EXAMPLE 1

The catalyst composition: $Mo_{12}V_2Sn_{2.2}Cr_{0.6}$ was prepared as follows.

To an aqueous solution containing 86.1 g of $(NH_4)_2Mo_2O_7$ and 3.2 g of $(NH_4)_2Cr_2O_7$ in 250 ml of distilled water, there were admixed 10 g of $NH_4VO_3$. This solution was brought up to 70°C and to it was then added an aqueous solution containing 32.7 g of $SnCl_4 \cdot 5 H_2O$ in 70 ml of distilled water. This mixture was then subjected to strong stirring, brought to boiling, and then evaporated to dryness.

The residue, after drying in an oven at 130°C, was calcined at 400°C for 5 hours in an air current. This residue was then ground and the fraction between 60 and 80 mesh (Tyler series) was collected.

7 ml of the catalyst were placed in the form of a fixed bed in a tubular steel reactor of 10 mm diameter, thermally stabilized by a bath of molten salts.

A gaseous mixture consisting of 4% by volume of acrolein, 56% of air and 40% of steam, was passed through the catalyst at a rate corresponding to a contact time of 1 second. The temperature was maintained at 300°C. The results obtained were as follows:

| | |
|---|---|
| Conversion of the acrolein | 98.8% |
| Selectivity of conversion to acrylic acid | 88.1% |

EXAMPLES 2-6

Catalysts having the compositions indicated in the following table were prepared, following the procedure of Example 1 and by using as nickel and manganese salts their respective nitrates.

The acrolein was oxidized in the presence of these catalysts as in Example 1 at the temperatures and contact times indicated in each case.

TABLE

| Example | Composition of the catalyst | Reaction temperature °C | Contact time sec. | Conversion to acrolein % | Selectivity acrylic acid % |
|---|---|---|---|---|---|
| 2 | $Mo_{12}V_6Sn_{2.2}Cr_{0.6}$ | 260 | 1 | 94.1 | 85.3 |
| 3 | $Mo_{12}V_6Sn_{2.2}Cr_{1.2}$ | 280 | 1 | 99.2 | 80 |
| 4 | $Mo_{12}V_4Sn_{2.2}Cr_{0.6}$ | 280 | 2 | 99.9 | 79.4 |
| 5 | $Mo_{12}V_6Sn_{2.2}Mn_{2.2}$ | 300 | 1 | 99.3 | 85 |
| 6 | $Mo_{12}V_6Sn_{2.2}Ni_{2.2}$ | 280 | 2 | 94.3 | 79.2 |

What is claimed is:

1. A process for the preparation of acrylic acid or methacrylic acid, comprising reacting in vapor phase acrolein or methacrolein with molecular oxygen or an oxygen-containing gas, at a temperature between 200° and 350°C, in the presence of a solid catalyst, and with a contact time between 0.5 and 5 seconds, wherein the catalyst consists essentially of molybdenum, vanadium, tin, and one of the elements selected from the class consisting of chromium, nickel and manganese, and oxygen chemically combined with the above-indicated elements, the atomic ratios of the elements being represented by the empirical formula:

$$Mo_{12}V_aSn_bX_cO_d,$$

wherein:
X is Cr or Ni or Mn;
$a$ is between 0.5 and 10;
$b$ is between 0.4 and 4;
$c$ is between 0.3 and 3.5; and
$d$ is a number that satisfies all the valency requirements of the other elements.

2. A process according to claim 1, wherein the catalyst is carried on a support.

3. A process according to claim 1, wherein the reaction is carried out in the presence of an inert gaseous diluent or water vapor.

* * * * *